United States Patent
Pease

(10) Patent No.: US 11,145,044 B2
(45) Date of Patent: Oct. 12, 2021

(54) SYSTEM AND METHOD FOR ANALYZING TEST DEVICES

(71) Applicant: PINQKERTON, Schiltigheim (FR)

(72) Inventor: Christopher Pease, Schiltigheim (FR)

(73) Assignee: PINQKERTON, Schiltigheim (FR)

( * ) Notice: Subject to any disclaimer, the term of this patent is extended or adjusted under 35 U.S.C. 154(b) by 0 days.

(21) Appl. No.: 16/384,439

(22) Filed: Apr. 15, 2019

(65) Prior Publication Data

US 2019/0318468 A1 Oct. 17, 2019

(30) Foreign Application Priority Data

Apr. 16, 2018 (FR) .................................. 1853321

(51) Int. Cl.
| | |
|---|---|
| *G06T 7/00* | (2017.01) |
| *G06T 7/62* | (2017.01) |
| *G06F 9/54* | (2006.01) |
| *G06K 9/00* | (2006.01) |

(52) U.S. Cl.
CPC ............ *G06T 7/0002* (2013.01); *G06F 9/542* (2013.01); *G06K 9/00536* (2013.01); *G06T 7/62* (2017.01)

(58) Field of Classification Search
CPC ......... G06T 7/0002; G06T 7/62; G06F 9/542; G06K 9/00536
USPC .................................................. 382/181–182
See application file for complete search history.

(56) References Cited

U.S. PATENT DOCUMENTS

| | | | | |
|---|---|---|---|---|
| 5,492,835 | A * | 2/1996 | Koenig | G01N 33/32 436/77 |
| 7,298,885 | B2 | 11/2007 | Green et al. | |
| 2001/0013249 | A1* | 8/2001 | Han | G01N 33/346 73/104 |
| 2003/0187586 | A1* | 10/2003 | Katzenmaier | G06Q 50/22 702/19 |
| 2004/0101189 | A1 | 5/2004 | Green et al. | |
| 2010/0254581 | A1* | 10/2010 | Neeser | A61B 5/0077 382/128 |
| 2011/0270087 | A1* | 11/2011 | Yoshida | A61B 8/06 600/443 |
| 2013/0162981 | A1* | 6/2013 | Emeric | G01N 33/48785 356/72 |
| 2013/0273666 | A1* | 10/2013 | Chen | G01N 21/8483 436/169 |

(Continued)

FOREIGN PATENT DOCUMENTS

| | | |
|---|---|---|
| EP | 2 453 242 A1 | 5/2012 |
| WO | 98/14777 A1 | 4/1998 |

(Continued)

*Primary Examiner* — Congvan Tran
(74) *Attorney, Agent, or Firm* — Nixon & Vanderhye

(57) ABSTRACT

The invention concerns in particular the analysis of a test device. After having obtained at least one image of a test device, the image comprising at least one representation of at least one portion of an observation surface and a visible reference having a predetermined format, the test device is identified according to the visible reference as well as a graphical element present in the portion of the observation surface. At least one geometrical feature of a graphical element identified according to at least the visible reference is then determined and the portion of the observation surface is analyzed according to an identification of the test device and at least one determined geometrical feature.

20 Claims, 11 Drawing Sheets

(56) References Cited

U.S. PATENT DOCUMENTS

| | | | |
|---|---|---|---|
| 2015/0241358 A1 | 8/2015 | Burg et al. | |
| 2016/0048739 A1* | 2/2016 | Burg | H04N 9/735 382/128 |
| 2017/0067832 A1* | 3/2017 | Ferrara, Jr. | G01N 21/78 |
| 2018/0190373 A1* | 7/2018 | Pulitzer | G16H 40/67 |
| 2018/0348137 A1* | 12/2018 | Schutze | G01N 33/5014 |

FOREIGN PATENT DOCUMENTS

| | | |
|---|---|---|
| WO | 2013/116831 A1 | 8/2013 |
| WO | 2014/025415 A2 | 2/2014 |
| WO | 2014/080212 A2 | 5/2014 |
| WO | 2014/099643 A1 | 6/2014 |
| WO | 2016/172527 A2 | 10/2016 |

* cited by examiner

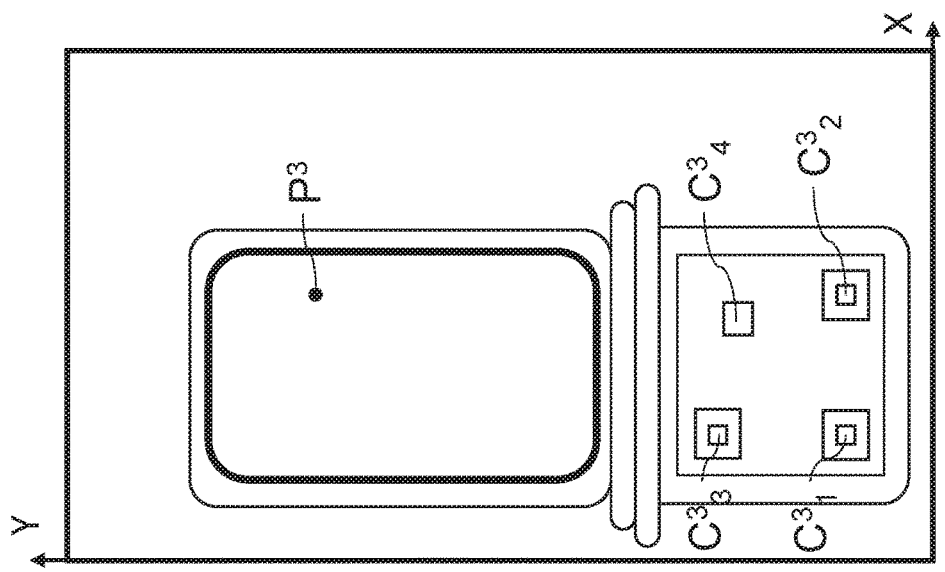
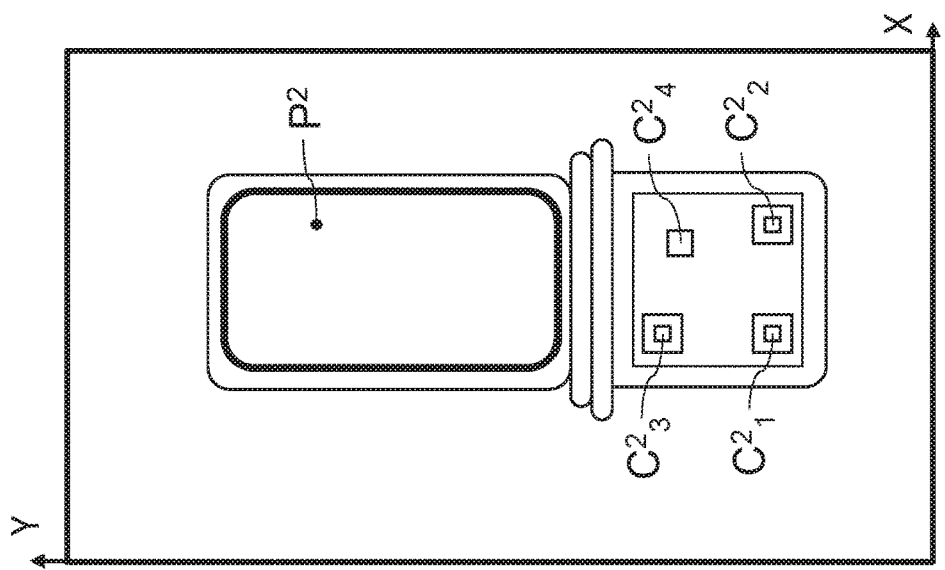
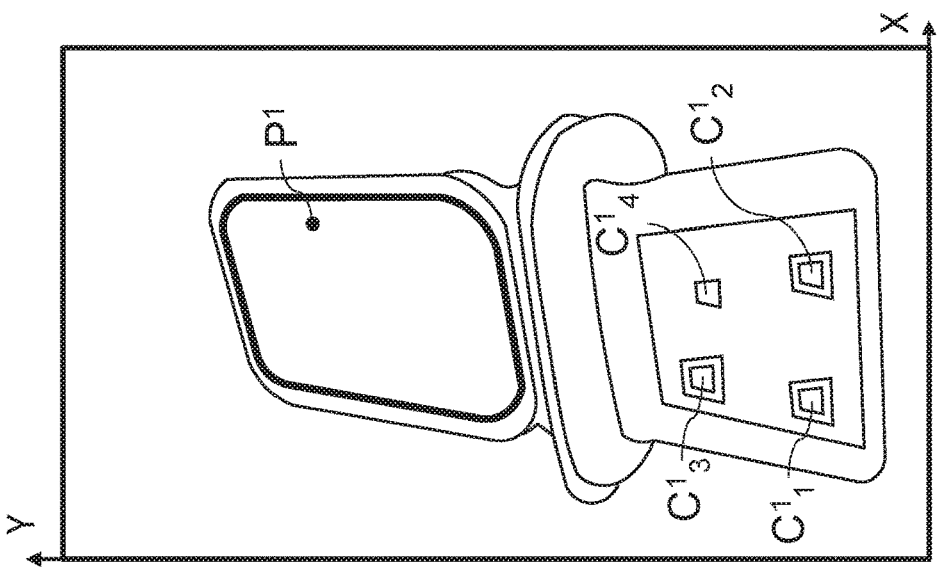

SYSTEM AND METHOD FOR ANALYZING TEST DEVICES

The present application claims the benefit of priority to French Application FR 1853321 filed with the French Intellectual Property Office on Apr. 16, 2018, the contents of which are incorporated herein by reference in their entirety.

FIELD OF THE INVENTION

The present invention concerns a system and a method for analysis of test devices, particularly biological or chemical test devices. In particular, the present invention can apply to test devices comprising biological growth media receiving for example food samples, samples of water resources, treated or effluent water, fuels or for instance environmental, laboratory or hospital samples.

BACKGROUND OF THE INVENTION

After incubation, colonies of microorganisms develop on a growth medium. These colonies are counted and classified. Once the number and types of colonies have been determined, a diagnostic can be made, it then being possible for the latter to be used, for example, for applying corrective measures directed to improving biological safety, production yields or the quality of products. It is noted here that biological contamination tests have become very important and mandatory in numerous fields.

Various techniques or apparatuses may be used to analyze test results in order to improve and increase reproducibility, reliability and traceability of the analysis of these tests.

Thus, by way of illustration, a sample, for example of liquid, may be placed on a biological growth medium of a test device, the test device then being inserted into an incubation chamber then, after incubation, introduced into a scanner to analyze the growth of colonies and count them automatically, reducing interpretation errors.

FIG. 1 represents a test and analysis system 10 according to the teaching of patent U.S. Pat. No. 7,298,885. The system 10 comprises a scanner 12, a screen 14 and a mounting 16 for receiving a test device 20 and introducing it into the body of the scanner 12. The device 20 has a test zone 22 and an identifier 24 for identifying the device 20 (in particular to determine the analysis to perform). The scanner 12 may then identify the type of device 20 thanks to the identifier 24 and automatically apply an appropriate analysis. The screen 14 makes it possible, for example, to display the test zone 22, the progression of the analysis (the remaining time), options that can be selected by a user (for example analysis parameters) and/or the results of the analysis by the device 20.

However, although addressing the issues, the system 10 has drawbacks, in particular in terms of costs, versatility (the system is only adapted to one type of specific device) and implementation (the system is not adapted to use in the field).

There is therefore a need for a system and a device for analysis of biological or chemical test devices, capable of being implemented easily and at lower cost, even in an environment with low resources, that is to say without a controlled environment or personnel trained in aseptic techniques.

SUMMARY OF THE INVENTION

Embodiments of the invention concern a method of analyzing a test device, the method comprising the following steps:

obtaining at least one image of a test device, the image comprising at least one representation of at least one portion of an observation surface and a visible reference having a predetermined format;

identifying a test device according to the visible reference;

identifying a graphical element in the at least one portion of the observation surface;

determining at least one geometrical feature of a graphical element identified according to at least the visible reference; and analyzing the at least one portion of the observation surface according to an identification of the test device and at least one determined geometrical feature.

The method according to the invention thus makes it possible to analyze test devices easily and at lower cost, for example biological or chemical test devices, in particular in environments that are not controlled and/or in the absence of qualified staff.

According to embodiments, the analysis step comprises a step of comparing the at least one determined geometrical feature with at least one geometrical feature of a graphical element identified in a portion of an observation surface represented in another image of a same test device.

According to embodiments, the method further comprises a step of projecting at least part of the at least one portion of the observation surface.

According to embodiments, the steps of identifying a test device, identifying a graphical element in the at least one portion of the observation surface and of determining at least one geometrical feature are repeated for at least one second image of the test device, the analysis step comprising a step of comparing at least one geometrical feature determined from a first image of a test device with at least one geometrical feature determined from a second image of the same test device.

According to embodiments, the method further comprises a step of determining a frame of reference according to the visible reference, the at least one geometrical feature being determined according to the determined frame of reference.

According to embodiments, the method further comprises a notification step giving notification that a new image has been obtained, the notification being given according to an identification of the test device determined from an image obtained previously.

According to embodiments, the notification step comprises a step of obtaining a test information item, the test information item being obtaining according to the test device identification determined from the image obtained previously.

According to embodiments, the method further comprises a step of storing the received image and the test device identification determined from the obtained image.

According to embodiments, the at least one geometrical feature comprises a size, a shape and/or coordinates.

The present invention also relates to a computer program comprising instructions adapted for the implementation of each of the steps of the method described earlier, when said program is executed on a computer. The advantages procured by that computer program are similar to those referred to above.

The invention is also directed to a system for analyzing a test device comprising means configured for the implementation of each of the steps of the method described above. The advantages procured by this system are similar to those referred to in relation to the method.

According to embodiments, the system comprises a device of smartphone type for image capture, image correction and analysis of images.

According to embodiments, the system comprises a first device for image capture and a second device for analysis of images, distinct from the first device.

Other advantages, objects and features of the present invention will emerge from the following detailed description, given by way of non-limiting example, relative to the accompanying drawings.

BRIEF DESCRIPTION OF THE DRAWINGS

Embodiments of the invention will now be described, by way of example only, and with reference to the following drawings in which:

FIGS. 6A, 6B and 6C illustrate a second example of standardization based on a predetermined format of a visible reference in order to enable the comparison of images of a test device obtained from several different points of view;

DETAILED DESCRIPTION OF THE INVENTION

Generally, the invention concerns a system and a method for analysis of test devices, in particular biological or chemical test devices, enabling for example the detection, the counting and/or the classification of colonies of microorganisms, using a same visible reference to identify the device (preferably making it possible to select a type of analysis to perform) and to analyze the device by analysis of images, without requiring a particular point of view on taking images of the device.

Embodiments of the invention are configured for the observation of the growth of colonies of microorganisms in order to analyze the development over time.

In some specific embodiments, an analysis unit, such as a smartphone or a tablet equipped with an image sensor, comprising a suitable software application, may be used to capture an image of the device, it being possible for the captured images to be processed and analyzed either by the analysis unit itself (if it has the necessary resources), or, for example, by a remote server to which the images or parts of images are transferred. When the processing and the analysis are carried out in a remote device, the analysis unit may consist of a simple device for taking digital shots.

Still in some specific embodiments, the analysis method is implemented in the analysis unit, with the use of a suitable application that is used for the capture of images, the standardization of the images acquired and their analysis. The user may furthermore be guided in the use of the application, for example to indicate the instants at which the images must be taken.

The test device is now described in more detail.

Figure 1:
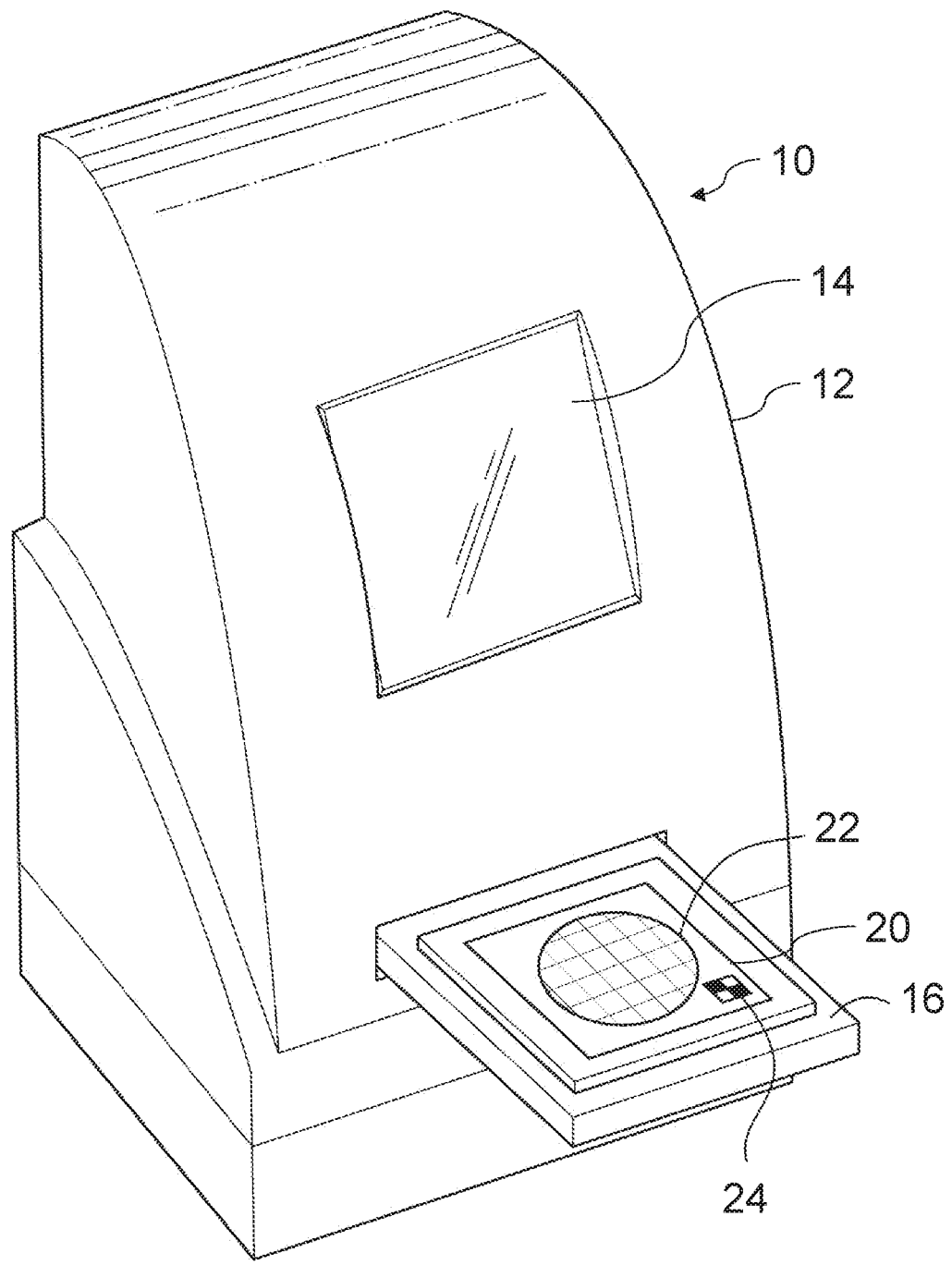
FIG. 1 represents a known system for analysis of test devices.
Figure 2A:
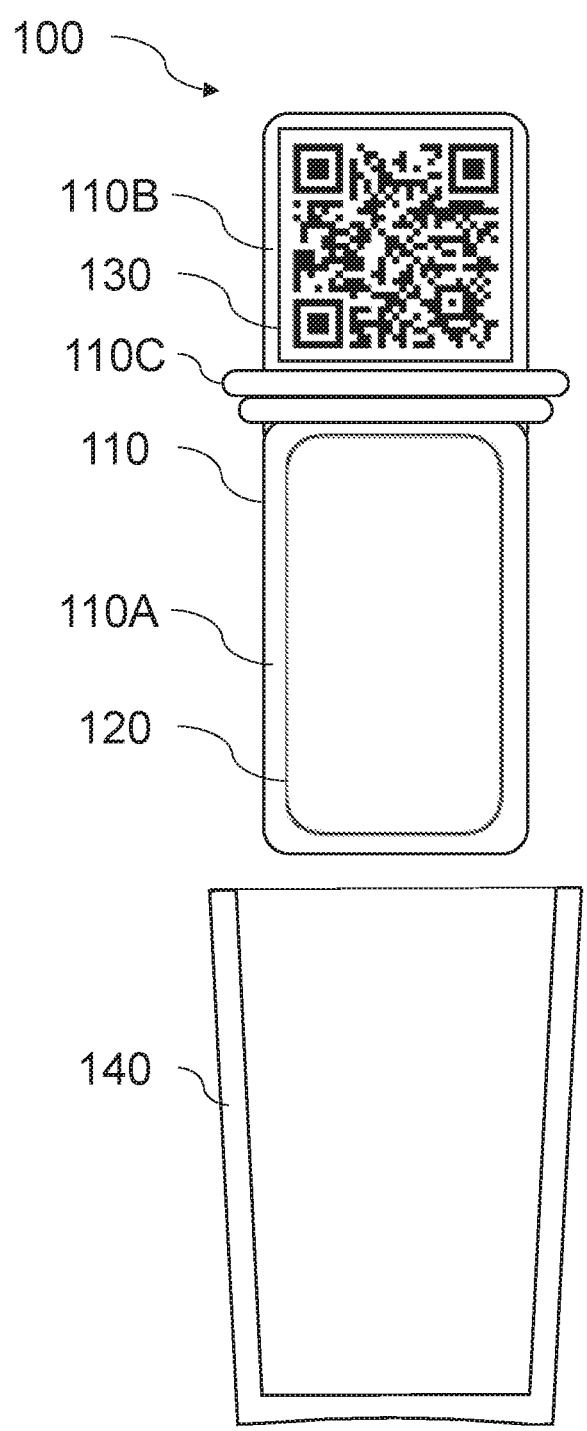
FIGS. 2A and 2B represent front views of a test device able to be used by an analysis system, according to embodiments, in two different configurations.
Figure 2B:
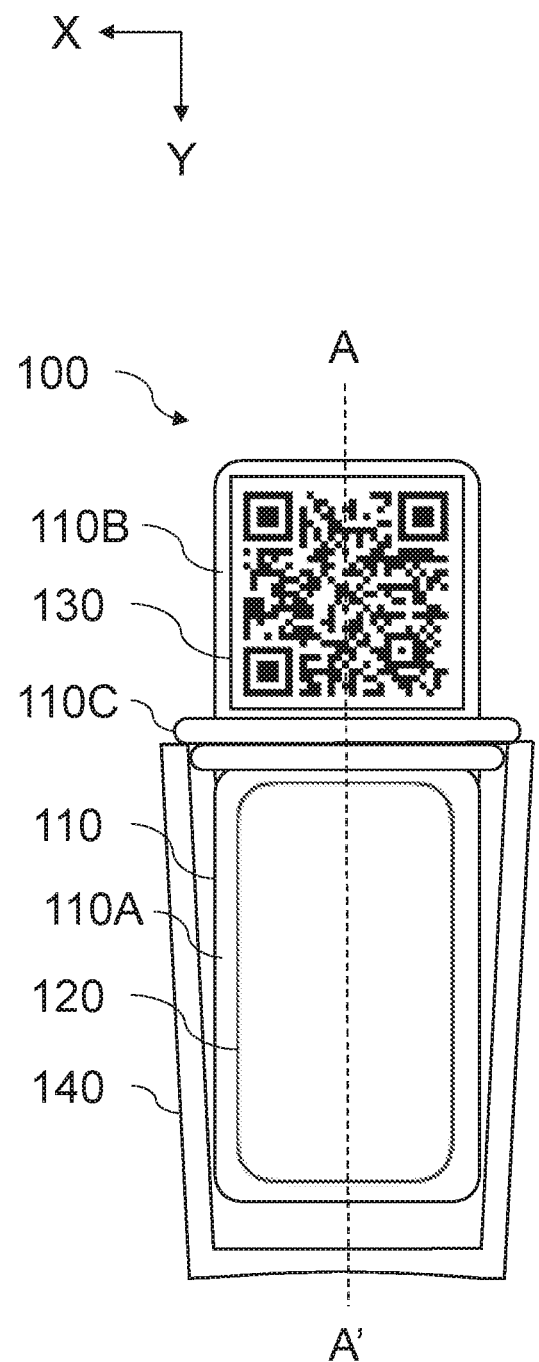

FIGS. 2A and 2B represent front views of a same test device 100 able to be used by an analysis system, according to embodiments, in two different configurations.

By way of illustration, the embodiments of the invention described below concern a device for biological growth of colonies of microorganisms. However, the invention is not limited to this field.

The test device 100 may have an open configuration, as illustrated in FIG. 2A or a closed configuration as illustrated in FIG. 2B.

Figure 3:
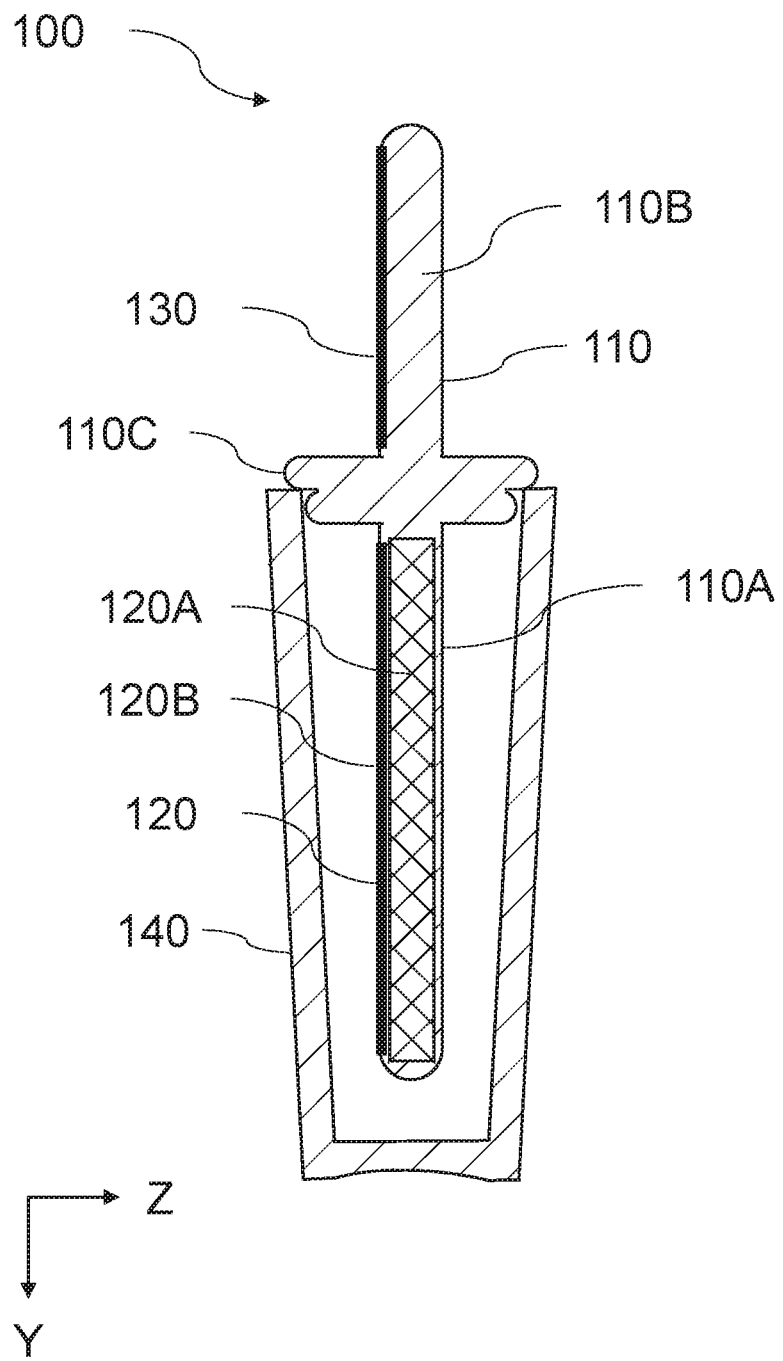
FIG. 3 represents a cross-section view, from the side, of the device illustrated in FIGS. 2A and 2B, in the configuration of FIG. 2B.

FIG. 3 represents a cross-section view, from the side, of the device 100 illustrated in FIGS. 2A and 2B, in the configuration of FIG. 2B.

As illustrated, the test device 100 comprises a carrier 110, a test zone 120, a visible reference 130 and a protective cover 140. The visible reference 130 enables identification of the test device 100 and standardization of an image representing that device, typically by determining a geometrical deformation of a representation of the test zone according to a predetermined format of the visible reference.

The carrier 110 comprises a first part 110A, called lower part, and a second part 110B, called upper part, separated by a closure stop 110C. The lower part 110A comprises the test zone 120. It is configured to be able to be inserted into the protective cover 140, as shown in FIGS. 2B and 3. It is noted here that the closure stop 110C may be an added-on part.

The protective cover 140 forms, with the carrier 110, a closed system enveloping and isolating the test zone 120 from the outside environment. The protective cover 140 is ideally transparent in order to enable regular image captures during the assay, without exposing the test zone 120 to the ambient air and, thus, to possible external contamination.

The upper part 110B may be used for the manipulation of the test device 100 without a user touching the test zone 120 and risking contamination of it. The visible reference 130 is arranged here on an upper part 110B, ideally above the stop 140 and outside the protective cover 140 in order for its reading not to be interfered with.

As illustrated in FIG. 3 representing a cross-section view on axis A-A' of FIG. 2B (i.e. in a plane YZ where the axis Y is oriented along the length of the device 100 and the axis Z is oriented along its depth), the test zone 120 here comprises a culture medium 120A, for example a nutritive medium, and an observation surface 120B. The culture medium 120A enables for example the culture of microorganisms and/or chemical and/or biological markers making it possible to reveal the presence of biological activities of the microorganisms and/or enabling to those microorganisms to be counted or classified.

According to embodiments, the test zone 120 and the visible reference 130 are arranged on the same face of the carrier 110, preferably in the same plane XY (the axis X being oriented along the width of the device 100 and the axis Y being oriented along the length of the device 100) or in parallel planes.

The observation surface 120B preferably covers the culture medium 120A which is, for example, planar and of square or circular shape. Still by way of illustration, the culture medium 120A may comprise a carrier such as a pad which may be constituted by cellulosic derivatives to retain a liquid or a gel enabling the culture of microorganisms.

The protective cover 140 may serve as a container to receive (preferably temporarily) a sample to analyze in which the test zone 120 may be immersed.

After the test zone 120 has been placed in contact with a sample to test and, as may be required, the excess sample has been removed from the test zone 120, the test device 100 is left to incubate for a certain time, the test zone 120 being protected in the protective cover 140. As described below, photographs of the device may be taken and analyzed according to the nature of the tests to perform.

The visible reference 130 is, for example, a visible identifier of QR code type (QR standing for Quick Response), a barcode or other identifier having a predetermined format. This format may be defined, for example, by the manufacturer of the device, the developer of an image processing software application according to some embodiments of the invention or by an analysis laboratory which receives images from the test device.

The visible reference 130 typically makes it possible to determine an analysis to perform. This reference may be common to several test devices or specific to each test device.

The identifier supplied by the visible reference 130, whether it be unique or common to several test devices, may be used as a database input in order to obtain and/or input information such as a type of microorganism, a manufacturer, a test protocol, a date of velocity, the name of a user, a date of use, etc. This database may be initially completed by the manufacturer of the test device and later enriched, when the test device is used. Several databases, corresponding to several test devices and/or to several types of information, may be used.

The visible reference 130 in addition makes it possible to standardize, if necessary, an image representing the test device by adapting, for example the scale factor and/or the perspective. For these purposes, the visible reference 130 is used as reference to determine a deformation or to define such a reference.

FIGS. 4A, 4B, 4C and 4D illustrate successive observations of a same test device during tests.

Figure 4A:
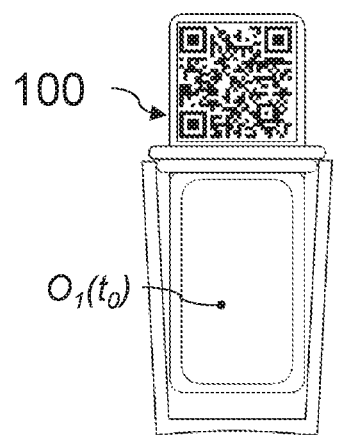
FIGS. 4A, 4B, 4C and 4D illustrate successive observations of a same test device during tests.

FIG. 4A illustrates the test device 100 at a time $t_0$, for example just after the test zone 120 of the device 100 has been placed contact with the sample to analyze. As illustrated in FIG. 4A, a patch denoted $O_1(t_0)$ is observed on the observation surface 120B at instant $t_0$. The features of this patch, for example its position, its size, its color and its shape are, preferably, recorded to enable its change to be analyzed.

Figure 4B:
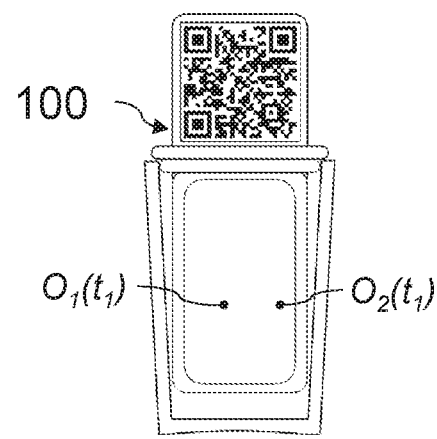

FIG. 4B shows the same test device 100 at a time $t_1$, for example 24 h after the time $t_0$. Again, the features of the patches observed, for example its position, its size, its color and its shape, may be recorded. According to the example illustrated in FIG. 4B, the patch $O_1$ has not changed between the instants $t_0$ and $t_1$ (i.e. the patches $O_1(t_0)$ and $O_1(t_1)$ are equivalent) and the patch $O_2$ has appeared on the observation surface 120B.

Figure 4C:
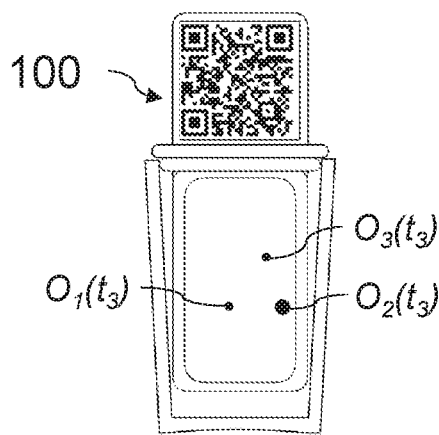

As illustrated in FIG. 4C, representing the same test device 100, the observation surface 120B shows, at an instant $t_2$, for example 48 h after instant $t_0$, the patches $O_1$ and $O_2$ already previously observed and a new patch $O_3$. The size of the patch $O_2$ has increased here relative to the observation made at instant $t_1$. Once again, the features of the patches observed, for example its position, its size, its color and its shape, are recorded here.

Figure 4D:
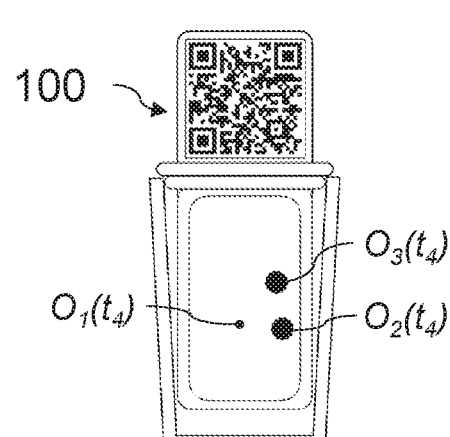

Still by way of illustration, FIG. 4D illustrates the same device 100 at an instant $t_3$, for example 72 h after instant $t_0$. According to this example, no new patch has appeared and the size of patches $O_2$ and $O_3$ has increased relative to the observation made at the instant $t_2$, the size of the patch $O_3$ having increased more rapidly than that of the patch $O_2$. Once again, the features of the patches observed, for example its position, its size, its color and its shape, are recorded here.

It is noted here that the features of the patch $O_1$ have not changed between the instants $t_0$ to $t_3$. It may therefore be concluded that the patch $O_1$ does not represent a colony of microorganisms. It may, for example, be dust. Furthermore, it may be considered that the patch $O_2$ represents a colony of microorganisms that are slow-growing (in the test conditions) and that the patch $O_3$ represents a colony of microorganisms that are fast-growing (still in the test conditions).

In general, the colonies of microorganisms appear in "waves" of time if there are sub-populations in the sample analyzed. If the image captures are fairly frequent, the detection of such waves may be an indication of the number of sub-populations, it being observed that there are required approximately one million microorganisms for a colony to be observable with the naked eye but that only a few thousands of microorganisms can generally be detected by an enlargement of ×10 (frequently available with the image sensors of a smartphone or a tablet).

The speed at which the size of a colony develops is an indication of the doubling time (in exponential phase) constituting an indication of the specific strain of the colony, it being observed that between the initial instant and the exponential phase, the bacteria generally have what is referred to as a latent phase during which they adapt to their new environment and multiply not at all or little.

The colonies are generally round but may be truncated, overlap or have different shapes (irregular, filamentous, rhizoid, etc.) according to the type of colony. Furthermore, the color of a colony is generally white but may be transparent, egg-shell colored, or of other color. Furthermore, the nutritive media may generate distinct colony colors or halos around the colonies. These aspects are well-known in the art. The analysis of an image may then include the evaluation of the shape, the color, the border, etc. Other optical techniques enable the relief and the texture of the colonies to be observed, for example by analysis of the deformation of a known pattern projected onto and reflected by the test zone 120. By a simple mirror system, it is possible to catch the reflected pattern and the visible reference 130 on the same image, then perform an analysis (as described for example with reference to steps 902, 905 and 906 of FIG. 9). The information on relief and textures is complementary to the information on size, speed of growth, color, transparency and similar properties and increases the capacity of the system to correctly classify the colonies.

According to embodiments, the user is called upon to capture the images which are then analyzed. He may thus be alerted at the start of the test of the number of images to take and the instants at which the images must be taken. He may furthermore be informed each time an image is to be taken.

As described above, the visible reference 130 makes it possible, further to the capture of an image to identify a test device 100 and, therefore, obtain characteristics about this test device and/or about tests in course, conducted or to conduct;

to identify an image part containing at least one portion of an observation surface 120B to analyze;

to establish a link between several acquired images to study a change in an observation surface; and/or to establish a link between points of an observation surface of several images, without requiring a predetermined point of view.

For these purposes, the visible reference 130 enables in particular the execution of a standardizing step to enable the images taken from different points of view to be compared. It is thus possible to standardize the image captures by the knowledge of the format of the visible reference 130.

Figure 5A:
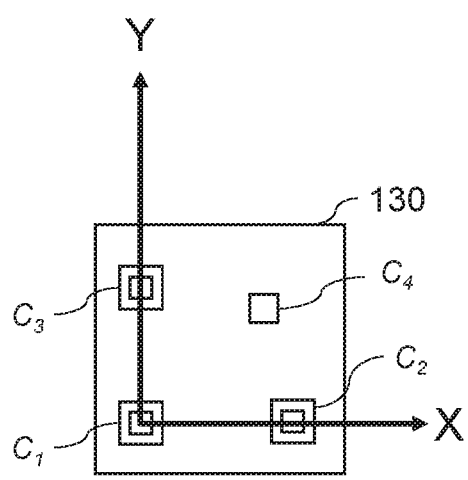
FIGS. 5A, 5B and 5C illustrate a first example of standardization based on a predetermined format of a visible reference in order to enable the comparison of images of a test device obtained from several different points of view.
Figure 5C:
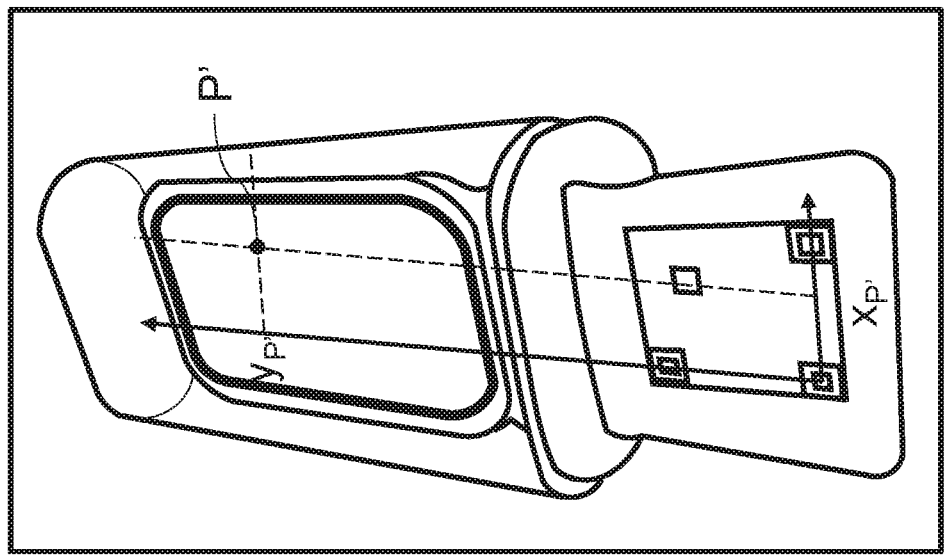
Figure 5B:
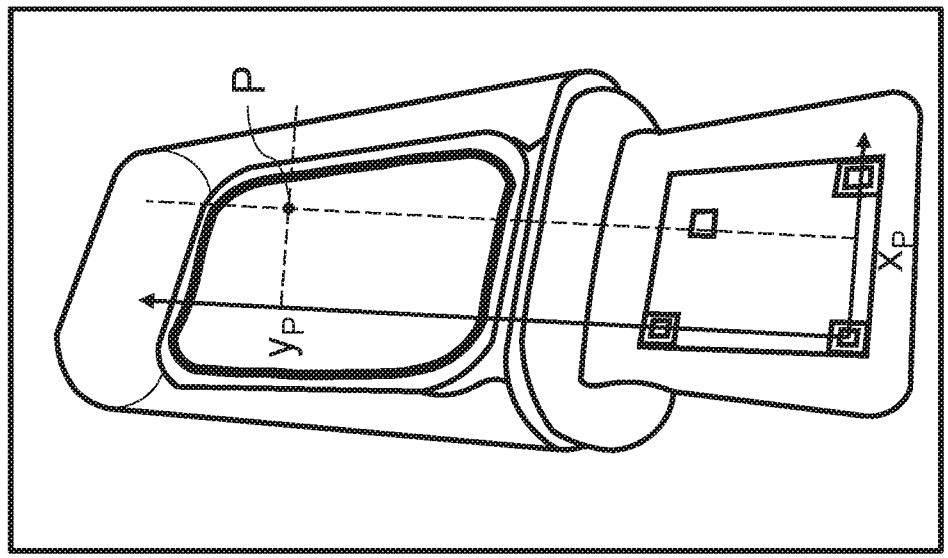

FIGS. 5A, 5B and 5C illustrate a first example of standardization based on a predetermined format of a visible reference in order to enable the comparison of images of a test device obtained from several different points of view.

According to this embodiment, it is assumed that the visible reference and the observation surface of the test device are disposed in a same plane.

FIG. 5A illustrates an example of a visible reference used as a geometrical frame of reference. The visible reference 130 used here is a QR code having a predetermined size. The QR code comprises three distinct squares $C_1$, $C_2$ and $C_3$, called position squares, disposed in the lower left, lower right and upper left corners, respectively, as illustrated. The QR code further comprises a fourth square $C_4$, called alignment square (the QR code may include several alignment squares according to the QR code version implemented). The alignment square or squares enable an image of the code to be corrected relative to the size, orientation and angle of image shooting.

The center of the position squares $C_1$, $C_2$ and $C_3$ is used to form a geometrical frame of reference in which may be expressed the coordinates of the visible reference points as well as the coordinates of the points of the observation surface of the test device (the visible reference and the observation surface here being placed in a same plane). As illustrated in FIG. 5A, the center of the position square $C_1$ forms the origin of the frame of reference, the center of the position squares $C_1$ and $C_2$ forms the x-axis as well as unit vector along that axis and the center of the position squares $C_1$ and $C_3$ forms the y-axis as well as the unit vector along that axis.

FIGS. 5B and 5C illustrate two images representing a test device 100 observed from two distinct points of view.

As illustrated, the identification of the visible reference 130 and of the position squares $C_1$, $C_2$ and $C_3$, according to standard image analysis techniques used, for example, for identifying QR codes, makes it possible to define a geometrical frame of reference linked to the visible reference 130, as described with reference to FIG. 5A The coordinates of points of the observation surface of the test device analyzed, coming from images obtained from different observation points, for example the point P and P' in FIGS. 5B and 5C, in this "standardized" frame of reference, may be compared with each other, for example to study the development of colonies of microorganisms.

FIGS. 6A, 6B and 6C illustrate a second example of standardization based on a predetermined format of a visible reference in order to enable the comparison of images of a test device obtained from several different points of view.

The visible reference used here is similar to that illustrated in FIG. 5A.

FIGS. 6A, 6B and 6C show three images representing a same test device observed from three different points of view at three different instants.

Considered here is a frame of reference rendered orthonormal and linked to the images analyzed. By way of illustration, it is considered here that the origin of the frame of reference is the lower left corner of the images and that the unit is the pixel.

Again, standard image analysis techniques that are implemented, for example, for identifying QR codes, may be used for identifying the position and alignment squares $C_1$, $C_2$, $C_3$ and $C_4$ and for determining the coordinates of their center, denoted $(x_1, y_1)$, $(x_2, y_2)$, $(x_3, y_3)$ and $(x_4, y_4)$, respectively, within a frame of reference linked to the image in which those squares are identified.

By determining the relation between each pair of points formed by these four points in two different images, it is possible to deduce therefrom the projection of one image to the other, and, therefore, to analyze the change in patches identified within an observation surface.

FIG. 6A represents a first image 600 of a test device obtained from a first point of view, in which it is possible to identify the position and alignment squares $C^1_1$, $C^1_2$, $C^1_3$ and $C^1_4$ and determine the coordinates of their center, denoted $(x^1_1, y^1_1)$, $(x^1_2, y^1_2)$, $(x^1_3, y^1_3)$ and $(x^1_4, y^1_4)$, respectively, within a frame of reference linked to the image in which those squares are identified. The image 600 for example was obtained at an instant $t_1$.

Similarly, FIG. 6B represents a second image 605 of the test device obtained from a second point of view, in which it is possible to identify the position and alignment squares $C^2_1$, $C^2_2$, $C^2_3$ and $C^2_4$ and determine the coordinates of their center, denoted $(x^2_1, y^2_1)$, $(x^2_2, y^2_2)$, $(x^2_3, y^2_3)$ and $(x^2_4, y^2_4)$, respectively, within a frame of reference linked to the image in which those squares are identified. The image 605 for example was obtained at an instant $t_2$.

Similarly again, FIG. 6C represents a third image 610 of the test device obtained from a third point of view, in which it is possible to identify the position and alignment squares $C^3_1$, $C^3_2$, $C^3_3$ and $C^3_4$ and determine the coordinates of their center. The image 610 for example was obtained at an instant $t_3$.

Based on the coordinates $(x^1_1, y^1_1)$ $(x^1_2, y^1_2)$, $(x^1_3, y^1_3)$ and $(x^1_4, y^1_4)$ and the coordinates $(x^2_1, y^2_1)$, $(x^2_2, y^2_2)$, $(x^2_3, y^2_3)$ and $(x^2_4, y^2_4)$, it is possible to determine the projection of any point of the image 600 into the image 605 and vice-versa.

Thus, for example, as described in the paper entitled "Perspective Correction Methods for Camera-Based Document Analysis", L. Jagannathan and C. V. Jawahar, Proceedings of First International Workshop on Camera Based Document Analysis and Recognition, August 2005, Seoul, Korea pp 148-154, the coordinates $(x^2_p, y^2_p)$ of point $P^2$ of the image 605 may be expressed on the basis of the coordinates $(x^1_p, y^1_p)$ of the point $P^1$ of the image 600 and a homograph H be characterized by the following homogeneous 3×3 matrix $$\begin{bmatrix} h_{11} & h_{12} & h_{13} \\ h_{21} & h_{22} & h_{23} \\ h_{31} & h_{32} & h_{33} \end{bmatrix}$$

in which the coefficient $h_{33}$ may be set to the value 1, $$x^2_p = \frac{h_{11}x^1_p + h_{12}y^1_p + h_{13}}{h_{31}x^1_p + h_{32}y^1_p + 1}$$

-continued $$y_p^2 = \frac{h_{21}x_p^1 + h_{22}y_p^1 + h_{23}}{h_{31}x_p^1 + h_{32}y_p^1 + 1}$$

the coefficients of the homograph may for example be calculated from the points $C^1_1$, $C^1_2$, $C^1_3$ and $C^1_4$ and $C^2_1$, $C^2_2$, $C^2_3$ and $C^2_4$, by solving the following equation system, $$\begin{bmatrix} x_1^1 & y_1^1 & 1 & 0 & 0 & 0 & -x_1^1 x_1^2 & -y_1^1 y_1^2 \\ x_1^1 & y_1^1 & 1 & 0 & 0 & 0 & -x_2^1 x_2^2 & -y_2^1 y_2^2 \\ x_1^1 & y_1^1 & 1 & 0 & 0 & 0 & -x_3^1 x_3^2 & -y_3^1 y_3^2 \\ x_1^1 & y_1^1 & 1 & 0 & 0 & 0 & -x_4^1 x_4^2 & -y_4^1 y_4^2 \\ 0 & 0 & 0 & x_1^1 & y_1^1 & 1 & -x_1^1 x_1^2 & -y_1^1 y_1^2 \\ 0 & 0 & 0 & x_1^1 & y_1^1 & 1 & -x_2^1 x_2^2 & -y_2^1 y_2^2 \\ 0 & 0 & 0 & x_1^1 & y_1^1 & 1 & -x_3^1 x_3^2 & -y_3^1 y_3^2 \\ 0 & 0 & 0 & x_1^1 & y_1^1 & 1 & -x_4^1 x_4^2 & -y_4^1 y_4^2 \end{bmatrix} \times \begin{bmatrix} h_{11} \\ h_{12} \\ h_{13} \\ h_{21} \\ h_{22} \\ h_{23} \\ h_{31} \\ h_{32} \end{bmatrix} = \begin{bmatrix} x_1^2 \\ x_2^2 \\ x_3^2 \\ x_4^2 \\ y_1^2 \\ y_2^2 \\ y_3^2 \\ y_4^2 \end{bmatrix}$$

Thus, the coordinates of a patch identified in an observation surface represented in a first image, for example the image 600, may be projected into the corresponding observation surface of a second image, for example the image 605, to enable a comparison of these coordinates with those of the corresponding patch of the observation surface represented in the second image.

Similarly, the coordinates of a patch identified in an observation surface represented in a first image may be projected into the corresponding observation surface of a third image, for example the image 610, to enable a comparison of these coordinates with those of the corresponding patch of the observation surface represented in the third image.

According to other embodiments, the visible reference is used to define the points that should be used to perform the projection, which may be points distinct from the visible reference.

It is also observed here that the visible reference may be used to identify the observation surface of the test device if the positions of the latter and of the visible reference are predetermined.

It is noted here that the analysis of an image may be interfered with by the analysis of artefacts such as dust deposited on the protective cover 140. In this case, several images of the test device may be obtained substantially at the same instant, from different points of view to detect the artefacts in order to be able to ignore them.

Figure 7A:
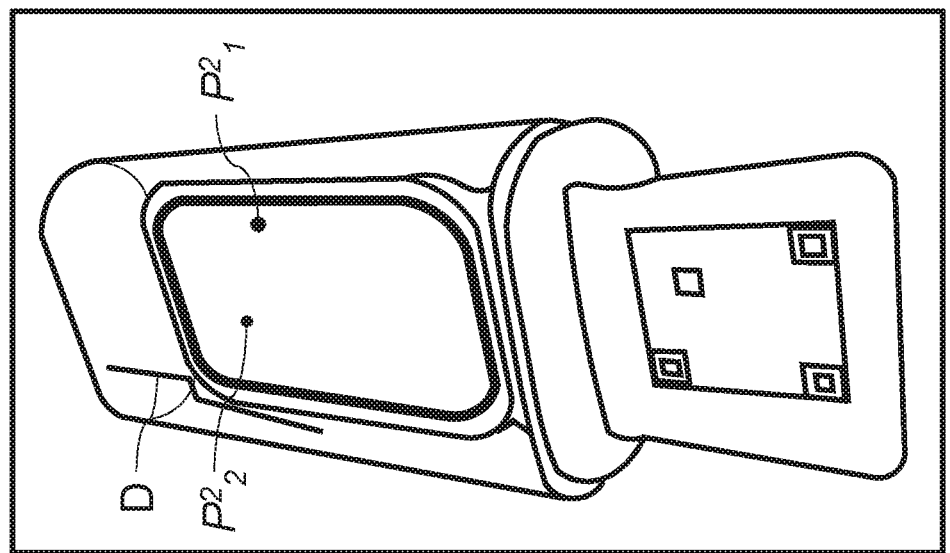
FIGS. 7A and 7B illustrate an example of correction of images according to a particular embodiment.
Figure 7B:
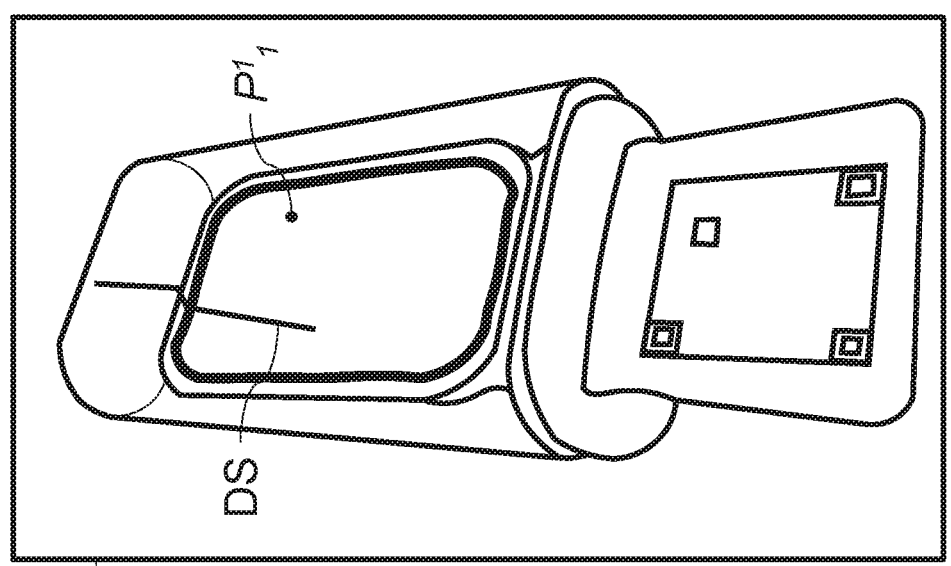

FIGS. 7A and 7B illustrate an example of correcting images according to a particular embodiment, between a first image 700 and a second image 705, respectively.

Such a correction may be carried out further to the detection of a suspicion of defect in an image or in a sequence of images, for example when an unexpected element is detected (for example, on account of its shape, its color, its size or its change over time).

FIGS. 7A and 7B show two images representing a same test device observed from two different points of view at two instants that are close to each other. The image represented in FIG. 7B is here taken further to the detection of a potential defect in the image represented in FIG. 7A.

More specifically, the analysis of the observation surface of the test device represented in FIG. 7A makes it possible to identify a patch $P^1_1$ and to detect a potential defect DS due, for example, to its shape and its color.

To determine whether it is a defect or a particular reaction in the test zone, another image is obtained from a different point of view, here the image represented in FIG. 7B. This image is acquired as soon as possible after obtaining the image on which a potential defect has been detected. For these purposes, the application may, after the detection of a potential defect, alert the user and suggest to him or her the acquisition of a new image to dispel the doubt.

The analysis of the observation surface of the test device represented in FIG. 7B enables the patches $P^2_1$ and $P^2_2$ to be identified but reveals no potential defect. It may thus be deduced that the potential defect identified on the observation surface of the test device represented in FIG. 7A is a defect that can be ignored.

According to embodiments, an analysis of the zone located around the observation surface of the test device represented in the image used to determine whether or not there is a defect may be carried out to identify the potential defect identified previously. The identification of this potential defect in the image of FIG. 7B, outside the observation surface, confirms that it is a defect linked to the protective cover 140. By way of illustration, the defect presented in FIG. 7 is a scratch or a mark on the outside surface of the protective cover 140. It could also, for example, be a droplet of condensation on the inside surface of the protective cover 140.

As illustrated in FIGS. 7A and 7B, the change in point of view moreover makes it possible to reveal, in the image of FIG. 7B, the patch $P^2_2$ which was concealed in the image of FIG. 7B.

Figure 8:
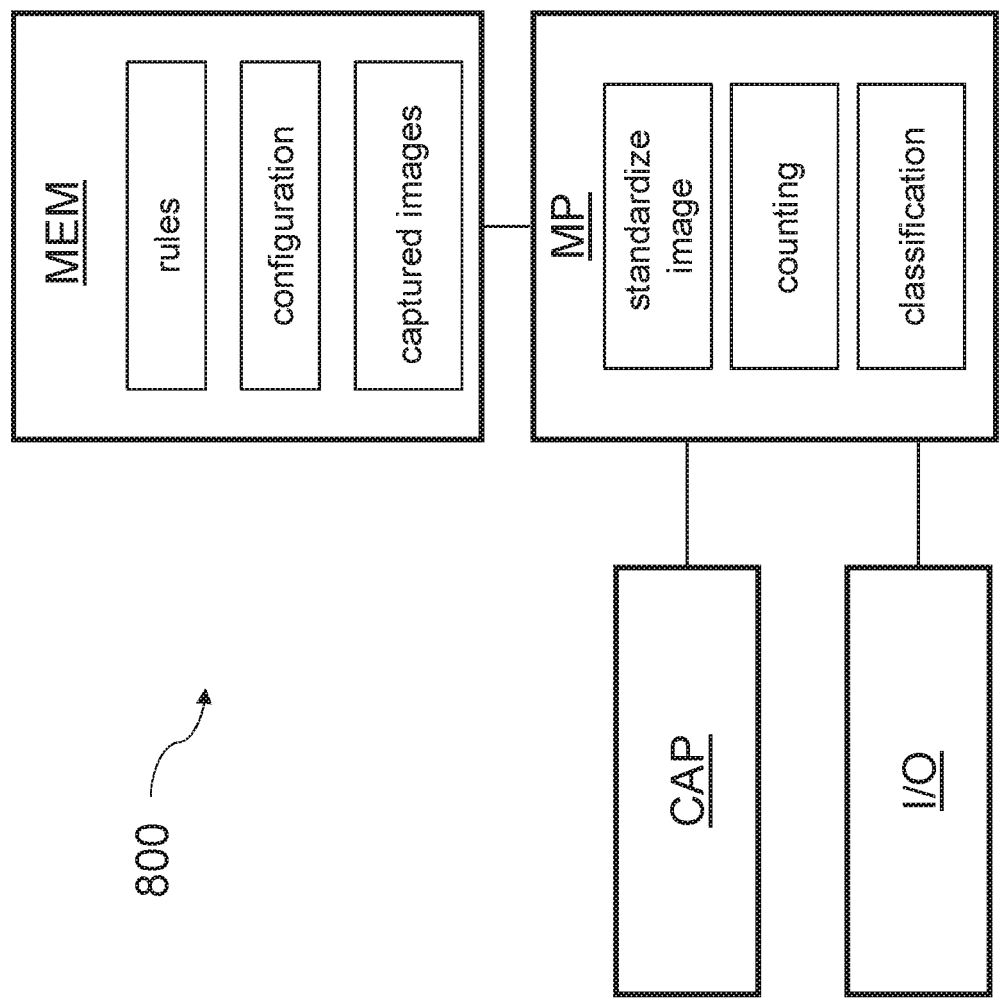
FIG. 8 represents an example of an analysis unit able to be used by an analysis system according to a particular embodiment.

FIG. 8 represents an example of an analysis unit 800 able to be used by an analysis system according to a particular embodiment. The analysis unit 800, for example a smartphone, here comprises an image sensor denoted CAP, a memory denoted MEM, a micro-processor denoted MP and an input/output module denoted I/O. These different components are here controlled by an application executed on the analysis unit.

The image sensor CAP is capable of taking images of the test device 100 with at least one portion of the observation surface 120B and the visible reference 130 with, preferably, a resolution making it possible to analyze the observation surface according to the type of test to perform. By way of illustration, the image capture is carried out by a user on recommendation by the application. A captured image is next transferred to the microprocessor MP for processing.

The memory MEM may be used to store the application as well as captured images. It may also be used to store, in the application or independently, rules for counting, classification and defect determination, incubation rules and rules for result validation. Alternatively, these rules may be stored in a remote system. The memory MEM may, for example, be updated by the final user, by a laboratory, by the software developer or by the manufacturer of the device 100.

The micro-processor MP receives an image acquired by the image sensor CAP. A first test is, preferably, carried out to determine whether the image acquired is exploitable, for example whether it is sufficiently clear, whether it comprises a representation of the visible reference and at least part of the observation surface. The visible reference is next, preferably, analyzed, for example to access and/or verify the characteristics of the test device 100, for example whether it has exceeded its expiry date and/or whether it is compatible with the envisioned test conditions. Characteristics of the analysis unit 700 may then be obtained, for example geo-location data, a time reference (present time) etc.

In a following step, the micro-processor MP performs a step of standardizing an image acquired according to a visible reference. As described above, such a step may in particular consist in defining a particular frame of reference in which are expressed the coordinates of the points analyzed or in the projection of the image (or certain points of the image) according to the visible reference and according to another image.

The acquired image is then analyzed, according to the determined standardization, for example in order to identify patches and compare them with patches identified in a preceding step.

Lastly, an input/output module I/O enables a user to control the analysis unit, for example to capture images, and to input information, for example comments. This module also enables notifications to be sent to the user, for example to ask the user to perform actions such as capturing an image, alert him or her of actions to come, for example warn the user that a new image should be captured within a time of n minutes or n hours (n typically being determined by the application according to the nature of the tests to perform), or give the user indications or information, for example indications regarding the test and/or the test device. The input/output module I/O may also be used to exchange data with a remote system, for example a server, for example to send test results. Such exchanges may be predetermined and/or may be concealed in relation to the user.

According to embodiments, one or more components of the analysis unit are absent or are not used, corresponding components of another unit being used. Thus, for example, image processing, for example a projection, which may require considerable computation resources, may be sent out to a remote unit, for example a remote server. The analysis unit may then be used as an image sensor and user interface.

As observed earlier, the application used may provide information to the user and guide the user in the tests to perform, for example to indicate to him or her how to obtain a sample and place the user in contact with the test zone of the test device, what the test conditions are, for example the time and temperature of incubation, assist him or her in shooting images, for example by means of indications for alignment or lighting. Examples of images may also be presented to the user to assist him or her.

Figure 9:
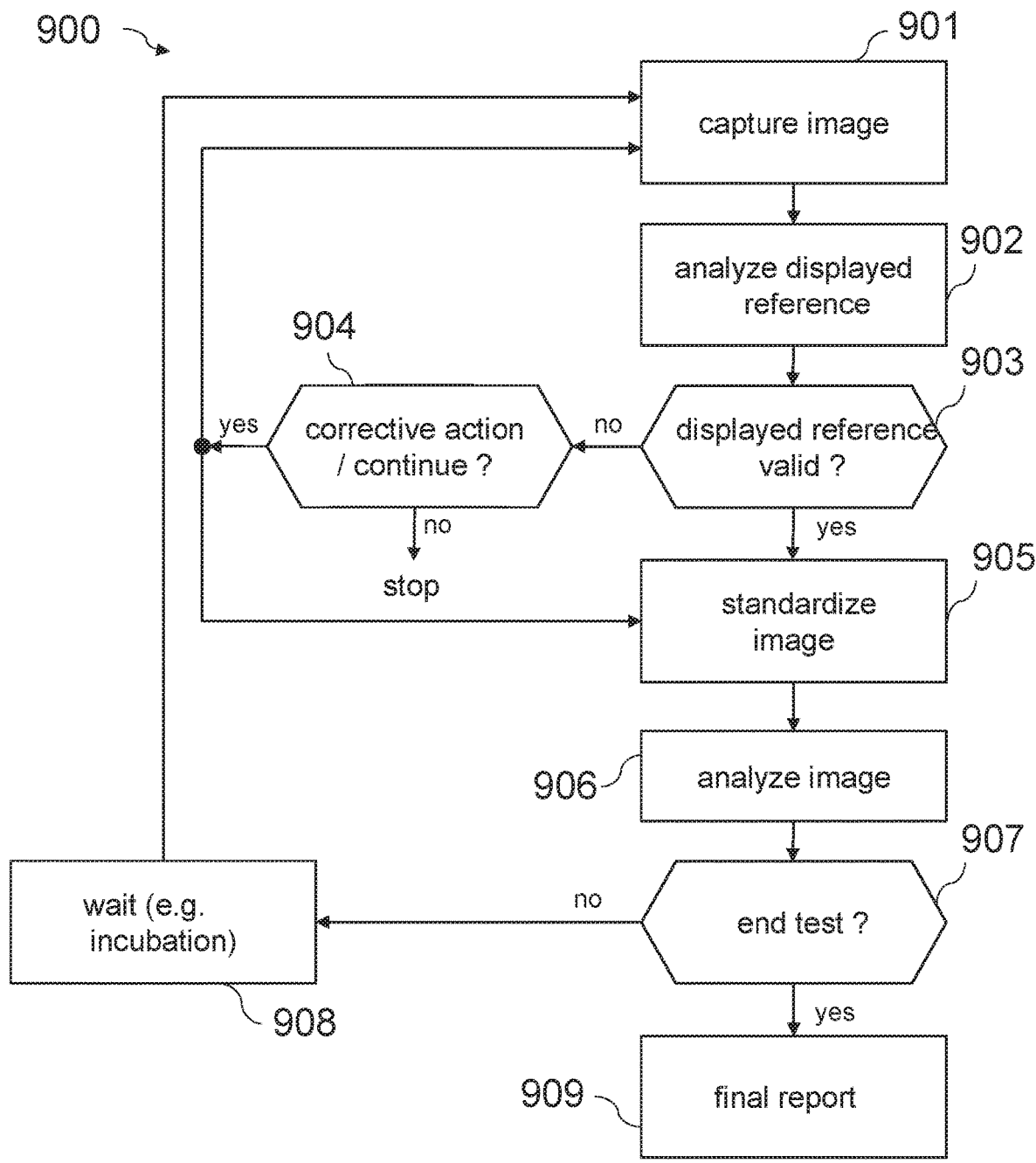
FIG. 9 illustrates steps of an example of an analysis method according to an embodiment.

FIG. 9 illustrates steps of an example of an analysis method according to an embodiment; The analysis method 900 here comprises steps 901 to 909. It may be implemented, for example, using the system 800 illustrated in FIG. 8, for example in the form of an application.

Step 901 is directed to the capture of an image of the test device 100. For these purposes, a notification may be sent to the user, after the latter has launched the application or has launched a new test, in order for him or her to capture an image of the test device. The first image captured may be obtained before a sample is presented to the test zone of the test device, for example to obtain a reference image of the test device, just after a sample is presented to the test zone of the test device to have a first image of a test start or after a certain incubation time.

Optionally, whether or not on recommendation by the application, the user may take other images, for example images representing the test environment or the source of the sample.

A quality test is advantageously carried out to check the quality of the acquired image, for example its clarity and/or the presence of a representation of at least part of the observation surface. If the quality is insufficient, for example with regard to a predetermined criterion, the user may be requested to capture another image.

According to embodiments, the acquired image is stored with additional information (metadata), such as an identifier of the image, an identifier of the analysis unit used to capture the image, an identifier of the user that captured the image, a notification of the source of the sample, a notification of temperature in the environment in which the test is made, geolocation information such as GPS data (GPS standing for global positioning system) and/or a notification of date and time of capture of the image.

In a following step (step 902), a first analysis of the acquired image is carried out to identify a visible reference having a predetermined format (for example a QR code or a barcode), using a standard algorithm. The identifier corresponding to the visible reference may be used to obtain data associated with that identifier in one or more databases. As described above, such data are, for example, a manufacturer, a test protocol and/or a validity date. A link is moreover established between that identifier, the acquired image and, preferably, at least some of the additional information or metadata referred to above. The image and this additional information may in particular be stored in the database or databases described above in relation to the identifier.

According to the illustrated example, a test is next carried out to determine whether the visible reference is valid, for example whether its format is in conformity with the expected format and/or whether it defines an expected identifier (step 903). In particular, it may be checked here that the identifier corresponding to the visible reference is valid, that is to say, for example, whether it corresponds to a test device that has not exceeded its expiry date and is consistent with the tests to perform. It may also be checked that the test zone is properly represented in the image or that there is prima facie, no artefact.

In the negative, it may be proposed to the user not to continue or to continue the analysis despite the detected anomaly or to perform a corrective action (step 904), for example take a new image. According to particular embodiments, an aid message is addressed to the user to indicate to him or her the nature of the anomaly (e.g. "device expiry date exceeded, continue?") and/or to indicate to the user the reason for the fault and aid him or her to overcome it (e.g. "proportion of the test zone insufficient: take a better-framed image" or "potential artefact: take a new image from a different angle").

If, on the contrary, the visible reference is valid, the acquired image may be analyzed. For these purposes, the visible reference is analyzed to determine a standardization for the acquired image (step 905). As described above, in particular with reference to FIGS. 5A to 5C and 6A to 6C, such standardization may in particular consists of determining a "normalized" frame of reference in which are expressed the coordinates of the points studied or to project the image in course of analysis or part of that image according to the visible marks of that image and the visible marks of an image acquired beforehand (of the same test device).

In a following step, the image is analyzed (step 906).

This analysis may be carried out on an analysis unit, for example a smartphone or a tablet, or on a system, for example a remote server. The analysis comprises the identification and the characterization of elements on an observation surface, typically the identification and the characterization of patches by their color, their shape and their size.

The analysis also preferably comprises, for the second image acquired and the following ones, the comparison of the features of the identified elements with those of elements identified on observation surfaces of earlier images. According to the standardization used, this analysis step comprises the comparison of features expressed on the basis of a frame of reference that is in common (or "normalized") or the comparison of features linked to a first image with features of a projection of a second image (or of part of the second image). For these purposes, one or more earlier images (or features obtained by analysis of those images) are obtained, according to the identifier of the test device. This analysis makes it possible for example to identify colonies of bacteria, count them and compare them between successive images.

In a following step (step 907), a test is carried out to determine whether the tests have been terminated or not, that is to say whether or not other images must be acquired and analyzed. The end of the test may be predetermined, for example according to a timescale, or linked to an observation, for example a number of colonies detected.

If the tests have not terminated, the preceding steps (steps 901 to 907) are repeated to process a new image. These steps are repeated after a predetermined time (step 908), for example an incubation time.

In the opposite case, if the tests have been terminated, a test report is, preferably, established (step 909). It contains, for example, statistics relative to the identified elements, relative to their features and their change.

There are other ways to implement the method 900 illustrated in FIG. 9. For example, the analysis of an observation surface represented in an image may begin after the capture of the latter, without awaiting the identification of the test device. Similarly, in some embodiments, the analysis of the images may be carried out after a high number of images, or all the images, have been acquired. It is also possible to analyze an image while capturing another image.

Figure 10:
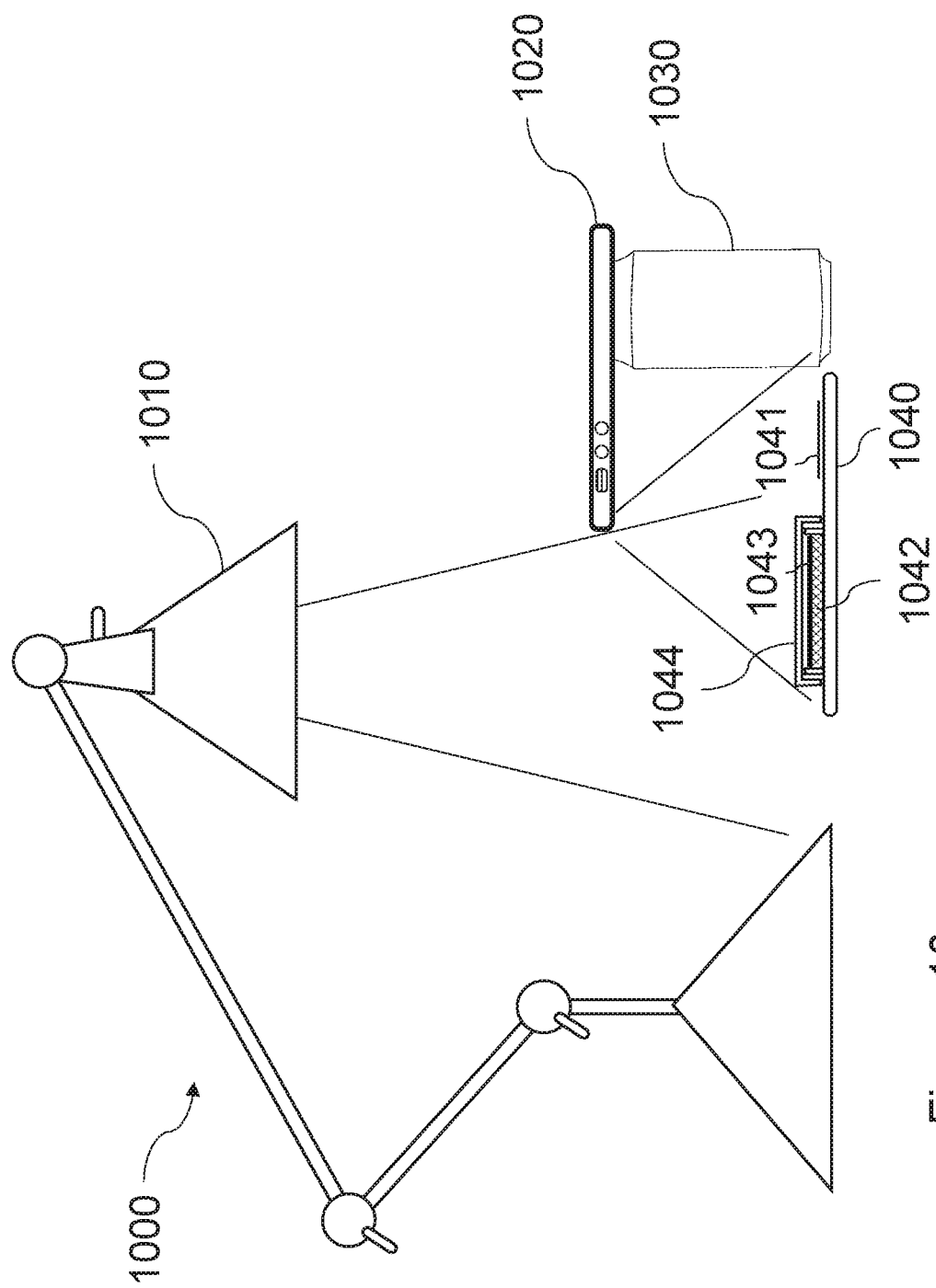
FIG. 10 represents an example of an analysis system according to a particular embodiment.

FIG. 10 represents an example of an analysis system 1000 according to a particular embodiment. The system 1000 is particularly suited to an implementation in varied environments.

According to the example illustrated here, the system 1000 comprises a source of artificial light 1010 (natural light is equally appropriate, or possibly better, than artificial light, but is not always available in sufficient quantity for a good shot), for example a desk lamp, an analysis unit 1020, for example a smartphone, a support 1030 for the analysis unit, for example a drinks can, and a test device 1040.

As illustrated, viewed from the side, the device 1040 comprises a visible reference 1041, a test zone 1042 and an observation surface 1043 protected by a protective cover 1044.

Figure 11:
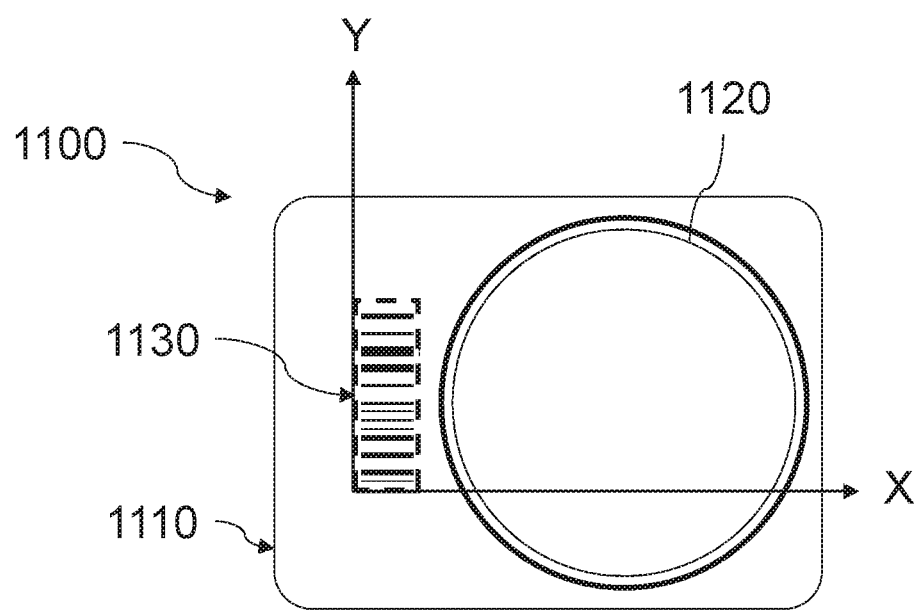
FIG. 11 represents a front view of a test device able to be used by a system according to embodiments.

FIG. 11 represents a front view of a test device 1100 according to another embodiment. The test device 1100 here comprises a carrier 1110, a test zone 1120 and a visible reference 1130. According to this example, the visible reference 1130 is a barcode of which the format may be used to define a frame of reference in which may be expressed the coordinates of the elements detected on the observation surface of the test zone 1120. In this example, the x-axis is defined as being the lower edge of the barcode and the y-axis as being the left edge of the barcode, the origin of the frame of reference being the bottom left corner of the barcode (when the device is viewed from the front, the test zone being placed on the right).

The test device 1100 may be used in the context of analysis systems and analysis methods described above.

Naturally, to satisfy specific needs, the skilled person will be able to apply modifications to the preceding description. The present invention is not limited to the described embodiments, other variants and combinations of features are possible.

The present invention has been described and illustrated in the present detailed description with reference to the appended Figures. However, the present invention is not limited to the embodiments presented. Other variants and embodiments may be deduced and implemented by the person competent in the field of the invention on reading the present description and appended Figures.

In the claims, the terms "comprise" or "include" do not exclude other elements or other steps. The indefinite article "a" does not exclude the plural. A single processor or several other units may be used to implement the invention. The different features presented and/or claimed may advantageously be combined. Their presence in the description or in different dependent claims, does not indeed exclude the possibility of combining them. The reference signs are not to be understood as limiting the scope of the invention.

The invention claimed is:

1. A method of analyzing a test device, the method comprising:
   obtaining at least one image of a test device, the image comprising at least one representation of at least one portion of an observation surface and a visible reference having a predetermined format;
   identifying a test device according to the visible reference;
   identifying a graphical element in the at least one portion of the observation surface;
   determining at least one geometrical feature of a graphical element identified according to at least the visible reference; and
   analyzing the at least one portion of the observation surface according to an identification of the test device and the at least one determined geometrical feature.

2. The method according to claim 1, wherein the analysis step comprises a step of comparing the at least one determined geometrical feature with at least one geometrical feature of a graphical element identified in a portion of an observation surface represented in another image of the same test device.

3. The method according to claim 2, further comprising a step of projecting at least part of the at least one portion of the observation surface.

4. The method according to claim 1, wherein the steps of identifying a test device, identifying a graphical element in the at least one portion of the observation surface, and of determining at least one geometrical feature are repeated for at least one second image of the test device, the analysis step comprising a step of comparing at least one geometrical feature determined from a first image of the test device with at least one geometrical feature determined from a second image of the same test device.

5. The method according to claim 4, further comprising a step of determining a frame of reference according to the visible reference, the at least one geometrical feature being determined according to the determined frame of reference.

6. The method according to claim 1, further comprising a notification step giving notification that a new image has been obtained, the notification being given according to an identification of the test device determined from an image obtained previously.

7. The method according to claim 6, wherein the notification step comprises a step of obtaining a test information item, the test information item being obtaining according to the test device identification determined from the image obtained previously.

8. The method according to claim 1, further comprising a step of storing the obtained image and the test device identification determined from the obtained image.

9. The method according to claim 1, wherein the at least one geometrical feature comprises a size, a shape and/or coordinates.

10. The method of claim 1, wherein, the visible reference is one of a Quick Response code and a barcode, and
the visible reference is used to determine an analysis to perform in said step of analyzing the at least one portion of the observation surface according to the identification of the test device and the at least one determined geometrical feature.

11. A computer program comprising instructions adapted for carrying out each of the steps of the method according to claim 1 when said program is executed on a computer.

12. A system for analyzing a test device, the system comprising a microprocessor configured for carrying out the steps of,
obtaining at least one image of a test device, the image comprising at least one representation of at least one portion of an observation surface and a visible reference having a predetermined format;
identifying a test device according to the visible reference;
identifying a graphical element in the at least one portion of the observation surface;
determining at least one geometrical feature of a graphical element identified according to at least the visible reference; and
analyzing the at least one portion of the observation surface according to an identification of the test device and the at least one determined geometrical feature.

13. The system according to claim 12, wherein the microprocessor is further configured so that the analysis step comprises a step of comparing the at least one determined geometrical feature with at least one geometrical feature of a graphical element identified in a portion of an observation surface represented in another image of the same test device.

14. The system according to claim 13, wherein the microprocessor is further configured for carrying out a step of projecting at least part of the at least one portion of the observation surface.

15. The system according to claim 12, wherein the microprocessor is further configured so that the steps of identifying a test device, identifying a graphical element in the at least one portion of the observation surface and of determining at least one geometrical feature are repeated for at least one second image of the test device, the analysis step comprising a step of comparing at least one geometrical feature determined from a first image of a test device with at least one geometrical feature determined from a second image of the same test device.

16. The system according to claim 15, wherein the microprocessor is further configured for carrying out a step of determining a frame of reference according to the visible reference, the at least one geometrical feature being determined according to the determined frame of reference.

17. The system according to claim 12, wherein the microprocessor is further configured for carrying out a notification step giving notification that a new image has been obtained, the notification being given according to an identification of the test device determined from an image obtained previously.

18. The system according to claim 17, wherein the microprocessor is further configured so that the notification step comprises a step of obtaining a test information item, the test information item being obtaining according to the test device identification determined from the image obtained previously.

19. The system according to claim 12, comprising a device of smartphone type for image capture, image correction and analysis of images.

20. The system according to claim 12, comprising a first device for image capture and a second device for analysis of images, distinct from the first device.

* * * * *